(12) United States Patent
Nowak et al.

(10) Patent No.: US 6,740,763 B1
(45) Date of Patent: May 25, 2004

(54) THIN-FILM EPOXIDATION OF AN UNSATURATED OIL OR ALKYL FATTY ACID ESTER

(75) Inventors: James A. Nowak, Naperville, IL (US); Thomas A. Zillner, Lake Bluff, IL (US); Leslie Patrick Mullin, III, Elmhurst, IL (US)

(73) Assignee: The C.P. Hall Company, Chicago, IL (US)

( * ) Notice: Subject to any disclaimer, the term of this patent is extended or adjusted under 35 U.S.C. 154(b) by 0 days.

(21) Appl. No.: 10/607,701

(22) Filed: Jun. 27, 2003

(51) Int. Cl.⁷ .................. C07D 301/16; C07D 301/12; C07D 301/14
(52) U.S. Cl. ................ 549/526; 549/525; 549/527
(58) Field of Search ............................ 549/526, 525, 549/527

(56) References Cited

U.S. PATENT DOCUMENTS 2,921,947 A * 1/1960 Millar et al. ............... 526/273

* cited by examiner

*Primary Examiner*—Ba K. Trinh
(74) *Attorney, Agent, or Firm*—Marshall, Gerstein & Borun LLP (57) ABSTRACT

A method of epoxidizing an unsaturated compound having a carbon-to-carbon double bond to form an oxirane ring across the double bond comprising adding to said unsaturated compound (a) an organic acid capable of being oxidized to form a peracid; (b) an oxidizing agent selected from hydrogen peroxide or acetaldehyde monoperacetate, or a combination thereof; and (c) with or without an acid catalyst selected from a mineral acid or styrene sulfonic acid, or a combination thereof to form a reactant mixture; and forming the reactant mixture in a film against a wall of a thin-film reactor that is at a temperature sufficient to form a peracid from the organic acid, and contacting the film of reactant mixture against the film reactor wall for a time sufficient for reaction of a portion of the peracid with the unsaturated compound to form an oxirane ring across a double bond of the unsaturated compound. In another embodiment, preformed peracid and unsaturated compound are added directly to the thin-film reactor.

20 Claims, 4 Drawing Sheets

FIG. 1B
IN-SITU EPOXIDATION

PRIOR ART

THIN-FILM EPOXIDATION OF AN UNSATURATED OIL OR ALKYL FATTY ACID ESTER

FIELD OF THE INVENTION

The present invention is directed to a method and apparatus for epoxidizing an unsaturated oil or an alkyl fatty acid ester, particularly an unsaturated vegetable oil, such as soybean oil, linseed oil, or an ester of tall oil fatty acids. More particularly, the invention is directed to a thin-film method of epoxidizing an oil or an alkyl fatty acid ester by combining the oil or alkyl fatty acid ester with a combination of acetic or formic acid, hydrogen peroxide and with or without an acid catalyst selected from a strong mineral acid, such as $H_2SO_4$ or phosphoric acid, or styrene sulfonic acid, to produce peracetic or performic acid, in-situ, for reaction (epoxidation) with the oil or alkyl fatty acid ester, in a thin-film reactor.

BACKGROUND OF THE INVENTION

Epoxy plasticizers, such as epoxidized unsaturated oils and, epoxidized alkyl fatty acid esters, particularly epoxidized soybean oil and epoxidized octyl esters of tall oil fatty acids can be manufactured by oxidation of either olefinic or aromatic double bonds, as follows:

Hydrogen peroxide and the unsaturated oil or the alkyl fatty acid ester alone do not react to any significant extent, and an organic peracid (usually acetic acid or formic acid) is necessary to shuttle the active oxygen from the aqueous phase to the oil phase. Once in the oil phase, the peracid adds oxygen across the carbon-to-carbon double bond and regenerates the original acid. On a commercial scale, epoxidation of soybean oil is achieved by oxidation of soybean oil with peracetic acid where the peracetic acid is derived from the oxidation of acetic acid with hydrogen peroxide, in-situ, in the presence of the soybean oil. In one process, peracetic acid generated in a process for oxidation of acetaldehyde to acetic acid has been isolated and used in the epoxidation process. This preformed peracetic acid can be handled, with proper precautions, in an inert solvent such as ethyl acetate or acetone. Others have found that an intermediate in the acetaldehyde oxidation process, acetaldehyde monoperacetate, also can be used as an epoxidizing agent. While oxidation of olefins by hydroperoxides is described in the literature, these prior art processes are far less efficient than the peracid processes.

Figure 1A:
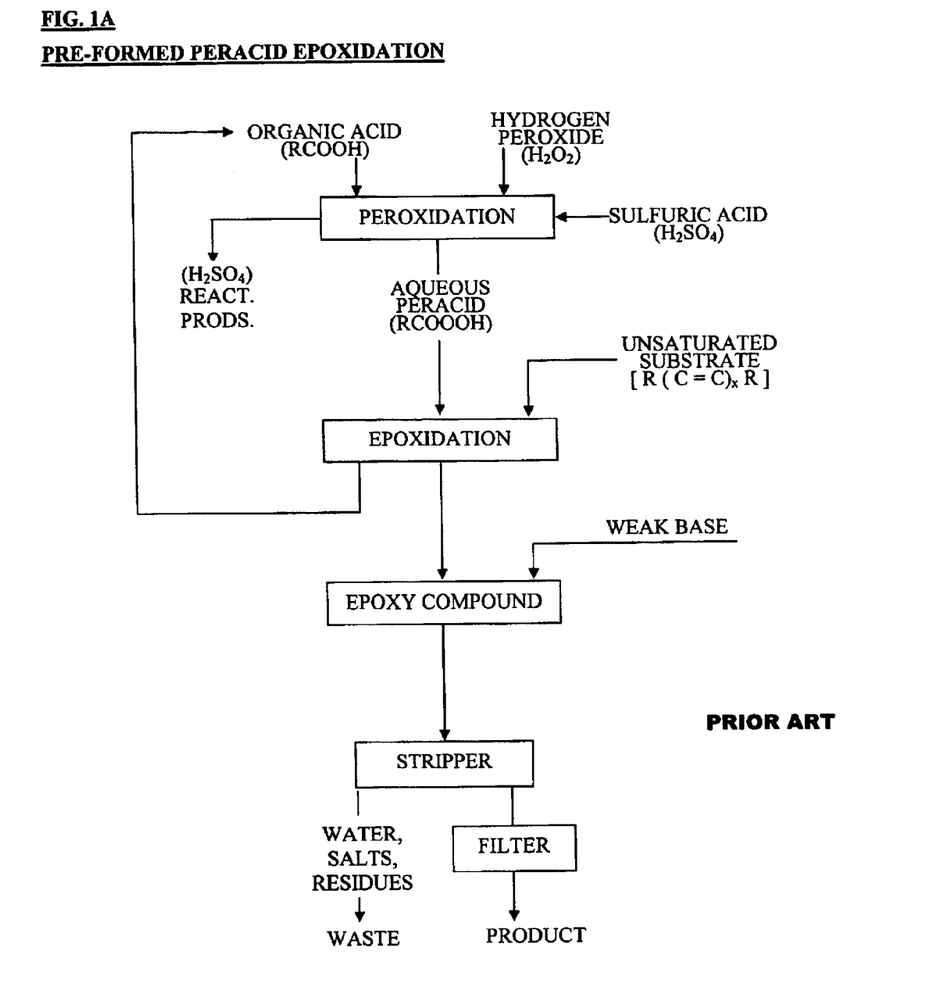
FIGS. 1A and 1B are a schematic flow diagrams of prior art preformed and in-situ peracid processes for epoxidizing an unsaturated substrate, such as soybean oil or an alkyl fatty acid ester.
Figure 1B:
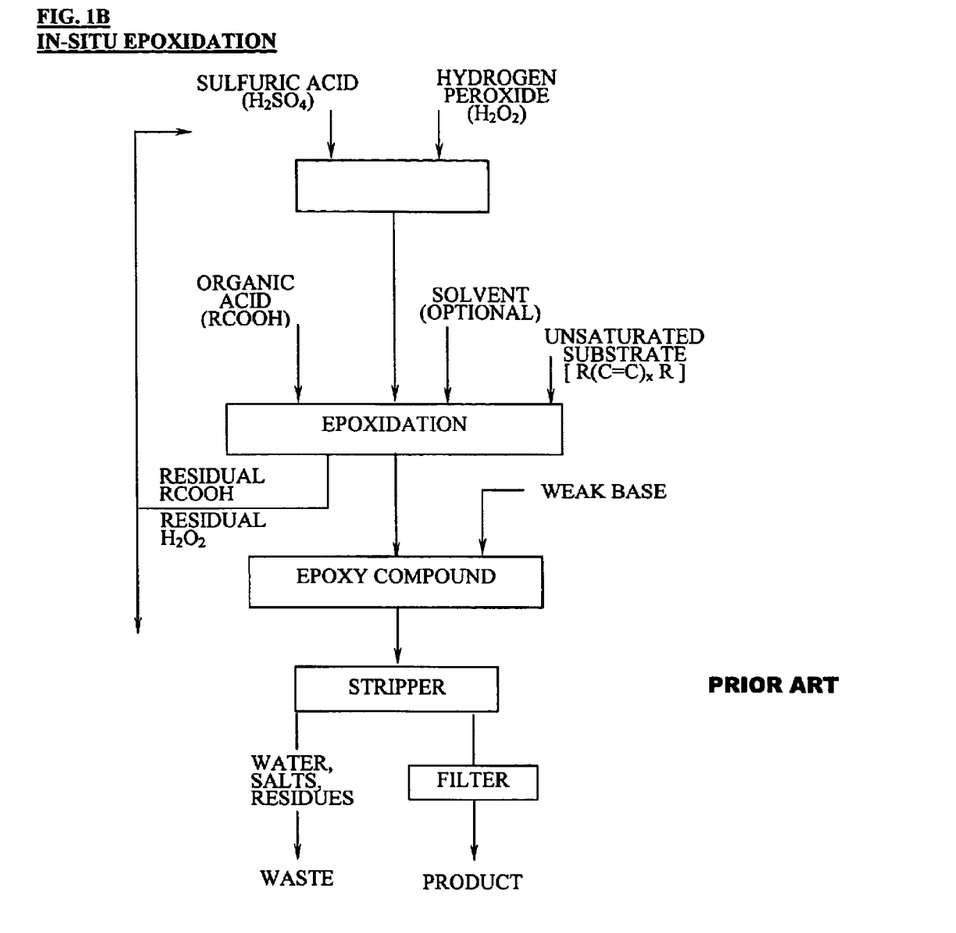

The epoxidation processes can be divided into two basic types. In the first, the peracid is preformed; in the second, the peracid is formed in-situ, that is in the primary reaction vessel. Representative schematics for the preformed and in-situ processes are shown in FIGS. 1A and 1B. The processes claimed herein are directed to a new and improved in-situ process.

Preformed Peracetic Epoxidation

The use of preformed peracetic acid results in epoxidation without catalyst at temperatures of 20 to 60° C. at atmospheric pressure, as follow:

The peroxidation of acetic acid with hydrogen peroxide is not efficient except at high molar ratios of acetic acid to hydrogen peroxide, resulting in large amounts of acetic acid to be recovered. In addition, concentrations of peracetic acid above 40 to 45 wt. % in acetic acid are explosive at epoxidation temperatures. Such processes require large volume production on an essentially continuous basis since the preformed peracid cannot be safely stored.

In-Situ Epoxidation—Acid Catalyzed

Experience has shown that the in-situ process is safer than processes using preformed peracids. In general, a peroxide solution (35% to 70% $H_2O_2$ in water) containing small quantities of a strong mineral acid catalyst, such as sulfuric acid or phosphoric acid, or styrene sulfonic acids, is added to a mixture of an epoxidizable substrate and acetic acid or formic acid at atmospheric pressure. As the reactants mix, the hydrogen peroxide and the acetic or formic acid react in the presence of the mineral acid catalyst to form the peracid, as follows:

To prevent uncontrolled exotherm and to optimize epoxidation, the peroxide solution is added in several increments with agitation, and the reaction temperature is maintained at 50° C. to 65° C. for periods of 10 to 40 minutes per incremental addition of peroxide. One of the biggest problems with this process is that only small batch quantities of peracid can be formed in the presence of the unsaturated substrate. The peracid reacts with the unsaturated portion of the molecule and is quickly depleted, preventing a build-up of detonatable quantities of peroxide compounds, as follows:

Further, significant problems are encountered in separation of the epoxidized substrate from the water, acid and peroxide remaining with the product after reaction. When the iodine number of the substrate has been reduced to the desired level, e.g, 0.5 to 10, the reaction is stopped and the epoxidized substrate is then difficult to separate from the aqueous layer since the aqueous layer contains a mixture of water, organic acid and some peroxide. Further, the epoxy layer contains acid-catalyst that must be neutralized by a mild base, and residual peroxide that must be decomposed. The epoxy then is washed and transferred to a stripper where water and non-product residues are removed.

Most, if not all of the above-identified difficulties of the known in-situ epoxidation processes are eliminated, or substantially reduced in accordance with the processes described herein.

SUMMARY

Figure 2A:
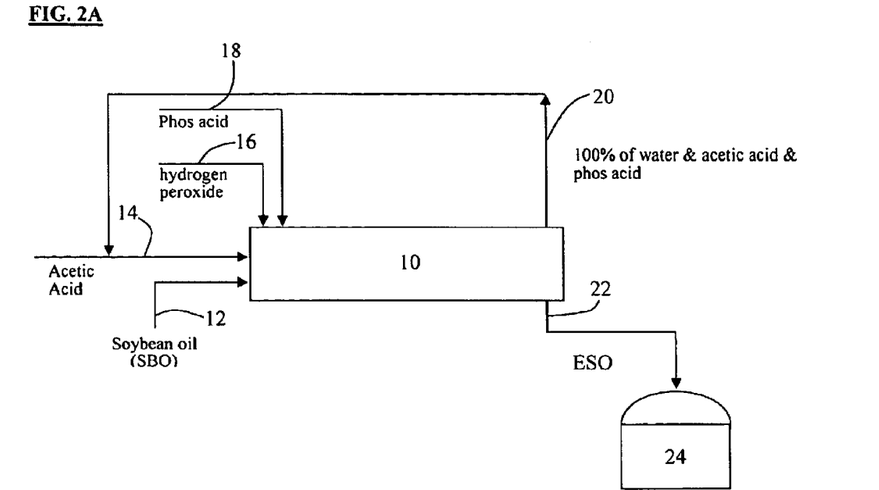
FIG. 2A is a schematic flow diagram of a preferred embodiment of a process, as described herein, for epoxidizing an unsaturated substrate, such as soybean oil or an alkyl fatty acid ester, by oxidation in the thin-film reactor.

The processes described herein take advantage of thin-film reactor apparatus for epoxidizing an unsaturated oil, such as soybean oil, linseed oil, or an alkyl ester of a fatty acid (hereinafter, the epoxidized unsaturated oil and/or the epoxidized alkyl fatty acid ester are referred to as the "epoxidized substrate"). In accordance with the processes described herein, the unsaturated substrate is reacted with a preformed peracid (FIG. 2B), e.g., peracetic acid or performic acid, in a thin-film reactor, or the peracid can be formed, in-situ, within the thin-film reactor, as shown in FIG. 2A, by reaction with an organic acid, such as acetic acid and/or formic acid, capable of being oxidized to a peracid, with or without an acid catalyst, such as a strong mineral acid, such as sulfuric or phosphoric, or styrene sulfonic acid, to accomplish oxidation of the organic acid to a peracid. In accordance with the preformed peracid embodiment, the peracid can be preformed in an ion-exchange bed and then fed to the thin-film reactor for reaction with the unsaturated substrate by ion-exchanging a mixture of and oxidizing agent, e.g., hydrogen peroxide, and an organic acid, particularly acetic acid or formic acid, with an ion-exchange resin, particularly an acid ion-exchange resin, such as a styrene sulfonic acid resin, e.g., AMBERLYST, or a methane sulfonic acid resin, e.g., AMBERLITE of Rohm & Haas, or a styrene divinyl benzene resin, e.g., DOWEX NCR of Dow Chemical. Both thin-film processes can be operated continuously while continuously stripping most of the water, acetic or formic acid, or peracid, and optional acid catalyst from the epoxidized product in the thin-film reactor. The thin-film reactor processes described herein can strip sufficient water, acid catalyst (if used) from the reaction product (epoxidized substrate) so that the epoxidized substrate requires little or no additional purification and the excess acetic or formic acid and the acid catalyst (if used) can be recycled to the continuous process.

Accordingly, one aspect of the processes described herein is the rapid removal of water, in the vapor phase, to allow increased rates of reaction (epoxidation) of unsaturated compounds.

Another aspect of the processes described herein is the elimination or substantial reduction of the neutralization, washing, decanting, and/or filtration steps needed with the presently practiced epoxidation processes.

BRIEF DESCRIPTION OF THE DRAWINGS

The above and other aspects and advantages of the methods and apparatus described herein are better understood with reference to the drawings and the following detailed description of the preferred embodiments, wherein.

DETAILED DESCRIPTION OF THE PREFERRED EMBODIMENTS

The thin-film processes described herein are useful for epoxidation of any unsaturated organic compound having at least one carbon-to-carbon double bond. The processes are particularly useful in the manufacture of epoxidized ester plasticizers, such as epoxidized alkyl fatty acid esters and epoxidized vegetable oils, particularly soybean oil and linseed oil.

Throughout this specification, ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The preferred alkyl fatty acid esters may be unsaturated compounds that can be epoxidized in accordance with the methods and apparatus described herein are the vegetable oils, particularly, soybean oil and linseed oil. The following vegetable oils (Table I) can be epoxidized in accordance with the methods and apparatus described herein to yield commercially acceptable products.

TABLE 1

Vegetable Oil Substrates For Epoxy Plasticizers

| Vegetable Oil | Iodine Number[1] | Number of Double Bonds Per 100 gms. | Theoretical Oxirane Oxygen, % |
|---|---|---|---|
| Linseed | 170–204 | 0.670–0.800 | 9.67–11.9 |
| Safflower | 140–150 | 0.552–0.591 | 8.11–8.63 |
| Soybean | 120–141 | 0.474–0.556 | 7.03–8.16 |
| Corn | 102–128 | 0.406–0.504 | 6.09–7.44 |
| Cottonseed | 99–113 | 0.390–0.445 | 5.87–6.65 |
| Rapeseed | 97–108 | 0.382–0.426 | 5.76–6.37 |
| Peanut | 84–100 | 0.331–0.394 | 5.03–5.93 |

[1]gms of $I_2$/100 gms of oil.

In addition to the unsaturated oils described above, another preferred class of esters which can be epoxidized in accordance with the methods and apparatus and apparatus described herein are monoesters, diesters, triesters, or mixtures thereof, that have radicals $R^1$ and $R^2$, straight chain or branched, wherein at least one of the radicals $R^1$ and/or $R^2$ have one, two or three double bonds in the hydrocarbon chain.

The preferred monoesters have a formula I, as follows:

(I)

wherein $R^1$ is a $C_3$–$C_{24}$ alkyl, preferably $C_3$–$C_{18}$ alkyl, more preferably $C_6$–$C_{18}$ alkyl, straight chain or branched, containing 1 to 3 carbon-to-carbon double bonds. $R^2$ is a $C_3$–$C_{24}$, preferably $C_6$–$C_{24}$, more preferably $C_8$–$C_{18}$ saturated hydrocarbon, or an unsaturated hydrocarbon having 1 to 6, preferably 1 to 3 carbon-to-carbon double bonds.

The preferred diesters have a formula II or III, as follows:

(II)

wherein n=3–24, preferably 6–18, and more preferably 3–10, and $R^3$ and $R^4$, same or different, are $C_3$–$C_{24}$ alkyl, preferably $C_3$–$C_{18}$ alkyl, more preferably $C_6$–$C_{18}$ alkyl radicals, straight chain or branched, containing 1 to 3 carbon-to-carbon double bonds, with at least one of the radicals $R^3$ and/or $R^4$ containing at least one carbon-to-carbon double bond.

(III)

wherein $R^5$ and $R^7$, same or different, are $C_3$–$C_{24}$ alkyl, preferably $C_6$–$C_{24}$ alky, more preferably $C_8$–$C_{18}$ alkyl, straight chain or branched, either saturated or containing 1 to 6, preferably 1 to 3, carbon-to-carbon double bonds;

$R^6$ and $R^8$, same or different, are $C_3$–$C_{24}$ alkyl, preferably $C_3$–$C_{18}$ alkyl, more preferably $C_6$–$C_{18}$ alkyl, straight chain or branched, saturated or unsaturated containing 1 to 3 carbon-to-carbon double bonds; and $R^{10}$ and $R^{11}$, same or different, are $C_3$–$C_{24}$ saturated hydrocarbon chains, preferably $C_3$–$C_{18}$, more preferably $C_6$–$C_{18}$, straight chain or branched; or unsaturated $C_3$–$C_{24}$ hydrocarbon chains, preferably $C_3$–$C_{18}$, more preferably $C_6$–$C_{18}$, straight chain or branched, containing 1 to 6, preferably 1 to 3, carbon-to-carbon double bonds. At least one of the radicals $R^6$, $R^8$, $R^{10}$ and/or $R^{11}$ of formula III should contain at least one carbon-to-carbon double bond.

The preferred triesters have a formula IV, as follows:

(IV)

wherein $R^{12}$, $R^{14}$ and $R^{18}$, same or different, are $C_3$–$C_{24}$ alkyl, preferably $C_6$–$C_{24}$ alkyl, more preferably $C_8$–$C_{18}$ alkyl, straight chain or branched, either saturated or containing 1 to 6, preferably 1 to 3, carbon-to-carbon double bonds;

$R^{13}$, $R^{15}$ and $R^{19}$, same or different, are $C_3$–$C_{24}$ alkyl, preferably $C_3$–$C_{18}$ alkyl, more preferably $C_6$–$C_{18}$ alkyl, straight chain or branched, saturated or unsaturated containing 1 to 3 carbon-to-carbon double bonds; and $R^{16}$, $R^{17}$ and $R^{20}$, same or different, are $C_3$–$C_{24}$ saturated hydrocarbon chains, preferably $C_3$–$C_{18}$, more preferably $C_6$–$C_{18}$, straight chain or branched; or unsaturated $C_3$–$C_{24}$ hydrocarbon chains, preferably $C_3$–$C_{18}$, more preferably $C_6$–$C_{18}$, straight chain or branched, containing 1 to 6, preferably 1 to 3, carbon-to-carbon double bonds. At least one of the radicals $R^{13}$, $R^{15}$, $R^{16}$, $R^{17}$, $R^{19}$ and/or $R^{20}$ should contain at least one carbon-to carbon double bond.

The fatty acid residues or hydrocarbon chains $R^2$, $R^5$, $R^7$, $R^{12}$, $R^{14}$ and $R^{18}$ of the esters of formulas I, II, III, and IV can be any $C_3$–$C_{24}$, preferably $C_6$–$C_{24}$, more preferably $C_8$–$C_{18}$, hydrocarbon chain, either saturated or containing 1 to 6, preferably 1 to 3, carbon-to-carbon double bonds, derived from animal or vegetable fatty acids such as butter; lard; tallow; grease; herring; menhaden; pilchard; sardine; babassu; castor; coconut; corn; cottonseed; jojoba; linseed; oiticica; olive; palm; palm kernel; peanut; rapeseed; safflower; soya; sunflower; tall; and/or tung. Examples are the hydrocarbon chain residues from the following fatty acids, where the number in parentheses indicates the number of carbon atoms, and the number of double bonds, e.g., ($C_{24-6}$) indicates a hydrocarbon chain having 24 carbon atoms and 6 double bonds: Hexanoic ($C_{6-0}$); Octanoic ($C_{8-0}$); Decanoic ($C_{10-0}$); Dodecanoic ($C_{12-0}$); 9-Dodecenoic (CIS) ($C_{12-1}$); Tetradecanoic ($C_{14-0}$); 9-Tetradecenoic (CIS) ($C_{14-1}$); Hexadecanoic (CIS) ($C_{16-1}$); 9-Hexadecenoic (CIS) ($C_{16-1}$); Octadecanoic ($C_{18-1}$); 9-Octadecenoic (CIS) ($C_{18-1}$); 9-Octadecenoic, 12-Hydroxy-(CIS) ($C_{18-2}$); 9, 12-Octadecadienoic (CIS, CIS) ($C_{18-2}$); 9, 12, 15 Octadecatrienoic (CIS, CIS, CIS) ($C_{18-3}$); 9, 11, 13 Octadecatrienoic (CIS, TRANS, TRANS) ($C_{18-3}$); 9, 11, 13 Octadecatrienoic, 4-Oxo (CIS, TRANS, TRANS) ($C_{18-3}$); Octadecatetrenoic ($C_{18-4}$); Eicosanoic ($C_{20}$); 11-Eicosenoic (CIS) ($C_{20-1}$); Eicosadienoic ($C_{20-2}$); Eicosatrienoic ($C_{20-3}$); 5, 8, 11, 14 Eicosatetraenoic ($C_{20-4}$); Eicosapentaenoic ($C_{20-5}$); Docosanoic ($C_{22}$); 13 Docosenoic (CIS) ($C_{22-1}$); Docosatetraenoic ($C_{22-4}$); 4, 8, 12, 15, 19 Docosapentaenoic ($C_{22-5}$); Docosahexaenoic ($C_{22-6}$); Tetracosenoic ($C_{24-1}$); and 4, 8, 12, 15, 18, 21 Tetracosahexaenoic ($C_{24-6}$).

Examples of particularly useful diesters of formula II include the unsaturated diester formed by the reaction of sebacic acid with oleyl alcohol:

Useful cyclic diesters falling within formula III include dirnerate ester structures formed by the reaction of a $C_{36}$ dimer acid derived from tall oil fatty acids and $C_3$–$C_{24}$, preferably $C_3$–$C_{18}$, more preferably $C_6$–$C_{18}$ alcohol, straight chain or branched, that are unsaturated, containing 1 to 3 carbon-to-carbon double bonds. Examples of such cyclic esters include the following structures, wherein the dimer acid corresponding to structure A is formed by self reaction of linoleic acid, the dimer acid corresponding to structure B is formed by reacting linoleic acid with oleic acid, and the dimer acid corresponding to structure C is formed by reacting linoleic acid with linolenic acid:

wherein each R, same or different, in formulas (A), (B), and (C) is a $C_3$–$C_{24}$ radical, preferably $C_3$–$C_{18}$, more preferably $C_6$–$C_{18}$, straight chain or branched, saturated or unsaturated containing 1 to 3 carbon-to-carbon double bonds. In formula B, at least one R has at least one carbon-to-carbon double bond. Another example of an unsaturated diester (dimerate ester) is an unsaturated diester formed by the reaction of a predominantly $C_{36}$ dimer acid reacted with 2-ethylhexyl alcohol. An additional unsaturated diester (dimerate ester) is formed by the reaction of a predominantly $C_{36}$ dimer acid with tridecyl alcohol.

A representative example of the triester (trimerate ester) of formula IV is the following structure (D);

and $C_{54}$ dimerate and trimerate esters (A), (B), (C) and (D), shown in the above structures, that is predominantly (more than 50% by weight) the $C_{36}$ dimerate esters (A), (B) and (C).

Commercially available blends of useful polybasic acids that can be reacted with $C_3$–$C_{24}$, preferably $C_3$–$C_{18}$, more preferably $C_6$–$C_{18}$ alcohols, straight chain or branched, saturated or unsaturated containing 1 to 3 carbon-to-carbon double bonds to produce the dimerate and trimerate esters, as blends, include the following: EMPOL® 1010 Dimer Acid; EMPOL® 1014 Dimer Acid; EMPOL® 1016 Dimer Acid; EMPOL® 1018 Dimer Acid; EMPOL® 1022 Dimer Acid; EMPOL® 1024 Dimer Acid; EMPOL® 1040 Trimer Acid; EMPOL® 1041 Trimer Acid; EMPOL® 1052 Polybasic Acid; and similar PRIPOL™ products from Uniqema as well as UNIDYME® products from Arizona Chemical.

Particularly useful unsaturated fatty acid esters are made by reacting any of the long chain mono, dimer and/or trimer acids with one or more straight chain or branched $C_3$–$C_{24}$, preferably $C_3$–$C_{18}$, more preferably $C_6$–$C_{18}$ alcohols to produce the esters of formulas I, II, III and IV. In addition, any of the above fatty acids can be reacted with polyhydric compounds, e.g., propylene glycol or ethylene glycol, to produce unsaturated bis-alkyl esters that can be epoxidized, as described herein to produce bisalkyl fatty acid esters having increased oxirane ring contents. The above dimer, trimer, and polybasic acids are produced by dimerizing, trimerizing, and polymerizing (oligomerizing) long chain carboxylic acids from the above-mentioned fatty acids. The fatty acids may be mixtures. Accordingly, the dimer acid produced by dimerizing a $C_{18}$ carboxylic acid (typically, a mixture of stearic, oleic, linoleic, and linolenic), after esterification, will result in a blend of numerous dimerate and trimerate esters in accordance with formulas III and IV, including unsaturated esters (i.e., the long chain esters may contain hydrocarbon chains having 1 to 6, generally 1 to 3, carbon-to-carbon double bonds). Any one, or any blend, of the esters of formulas I, II, III and/or IV, can be epoxidized, forming an oxirane ring across any or all of the carbon-to-carbon double bonds in accordance with the processes described herein.

In accordance with the flow diagram shown in FIG. 2A, an unsaturated substrate, e.g., an alkyl fatty acid ester or an unsaturated vegetable oil, is fed to a thin-film reactor 10, e.g., a ROTOTHERM® thin-film processor, or a spinning disc reactor, or a wiped film evaporator, or a thin-film evaporator, through reactant feed conduit 12 and, simultaneously, epoxidizing reactants are fed to the thin-film wherein each $R^1$, $R^2$, and $R^3$, same or different, is a $C_3$–$C_{24}$ radical, preferably $C_3$–$C_{18}$, more preferably $C_6$–$C_{18}$, straight chain, or branched, saturated or unsaturated containing 1 to 3 carbon-to-carbon double bonds.

Figure 2B:
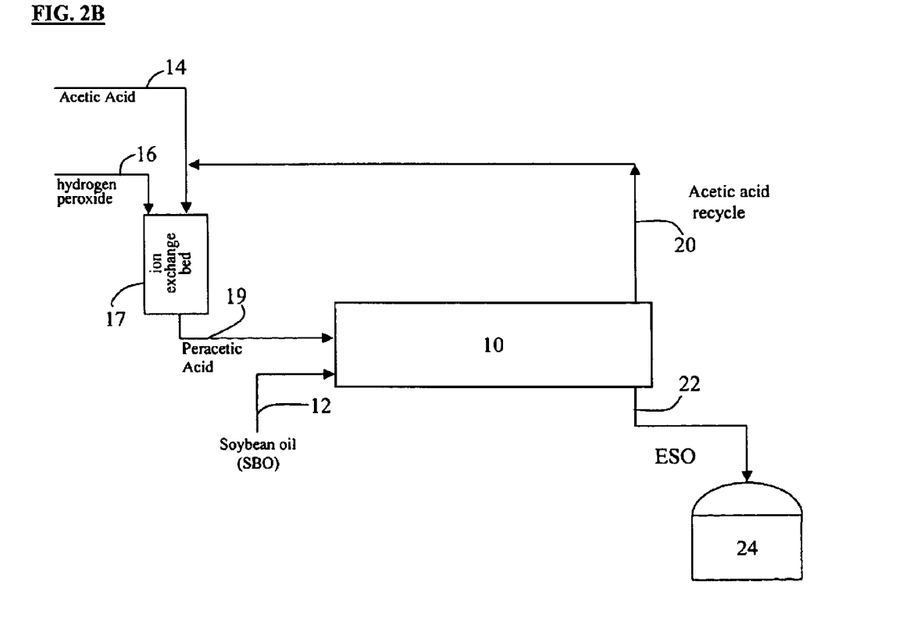
FIG. 2B is a schematic flow diagram of another embodiment (preformed peracid) of a process for epoxidizing an unsaturated substrate in a thin-film reactor.

A particularly useful blend of long chain esters is formed from blends of mono, dimer, and trimer acids, for example, products having CAS#: 61788-89-4. Esters prepared from such products are blends including, primarily, the above $C_{36}$ reactor 10 through conduit 12, or through separate feed conduits 14, 16, and 18. The reactants include an organic acid capable of being oxidized with $H_2O_2$ and/or acetaldehyde monoperacetate to form a peracid, e.g., acetic acid and/or formic acid, preferably acetic acid; an oxidizing agent capable of oxidizing the organic acid to a peracid, preferably hydrogen peroxide and/or acetaldehyde monoperacetate, through feed conduit 16; and with or without an acid catalyst, selected from a mineral acid, such as sulfuric acid and/or phosphoric acid, and/or styrene sulfonic acid. Preferably, the reactants are combined and homogenized prior to being added to the thin-film reactor 10 as a reactant mixture through a single feed conduit, e.g., 12. The thin-film reactor 10 is maintained at a temperature in the range of about 65° F. to about 150° F., preferably in the range of about 100° F. to about 130° F., and at a pressure of about 25 to 400 mm Hg absolute. As shown in FIG. 2B, the reactants necessary to form a peracid are fed to an ion-exchange bed 17, and the peracid product is fed to the thin-film reactor 10, through conduit 19.

Water contained in the reactants and reaction water is evaporated during processing, together with the acid catalyst (if used) and any excess acetic and/or formic acid is removed from the thin-film reactor 10 through overhead conduit 20 for recycle to a feed conduit, e.g., 12 of the thin-film reactor 10. The epoxidized product, e.g., epoxidized soybean oil (ESO), is removed from a bottoms product discharge conduit 22 for collection in product collection vessel 24.

Figure 3A:
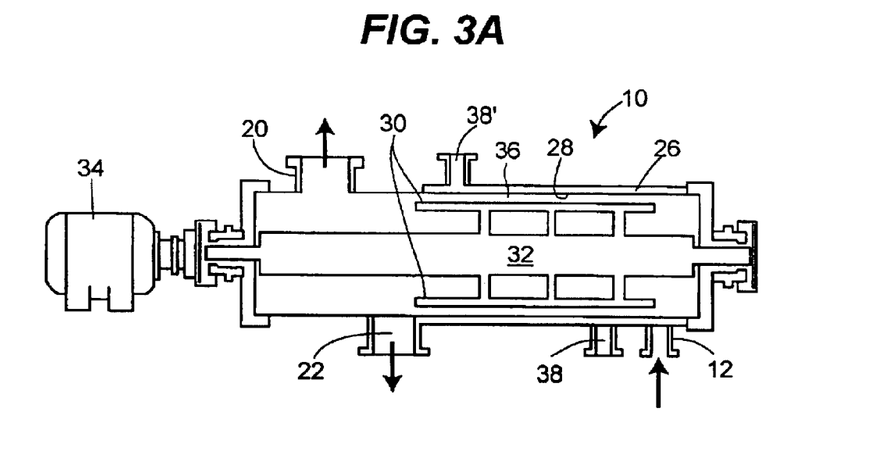
FIGS. 3A and 3B are cross-sectional views of a typical thin-film reactor, showing co-current flow of reactants (FIG. 3A) and counter-current flow of reactants FIG. 3B).
Figure 3B:
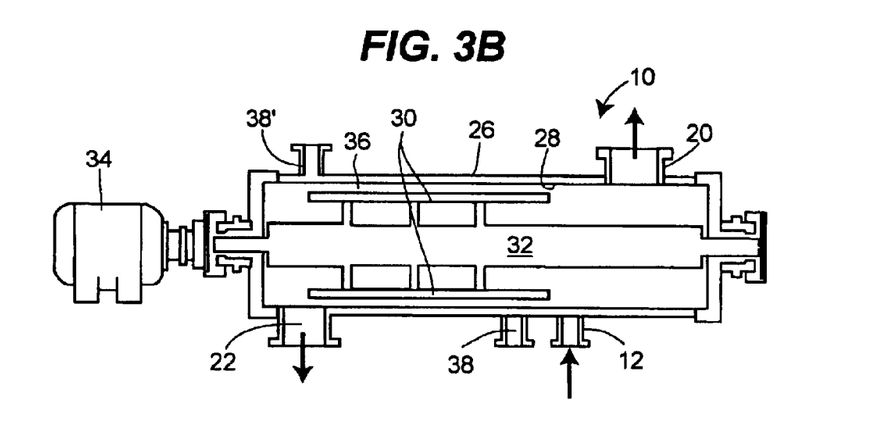

A typical thin-film reactor 10, best shown in FIGS. 3A and 3B, includes a horizontally disposed cylindrical casing 26, preferably formed from stainless steel, nickel, INCONEL®, MONEL®, HASTELLOY®, or titanium, having a smooth inner process wall 28 on which the reactants form a thin-film as a result of centrifugal force exerted by rotor blades 30. The rotor blades 30 are connected to a horizontal shaft 32 rotated by motor 34. Inner process wall 28 is heated to a temperature in the range of about 65° F. to about 150° F., preferably about 100° F. to about 130° F. to initiate the epoxidation reaction. The smooth inner process wall 28 is heated by circulating a heating medium 36, e.g., THERMINOL®, through a cylindrical passageway disposed adjacent to a portion of the inner process wall 28 that is adjacent to the rotor blades 30. The heating medium 36 is fed to the reactor 10 through heating medium conduit 38 and the heated medium recirculates through conduit 38' to heat the reactants to the desired reaction temperature. Once the reaction begins, it is very exothermic. The inner process wall 28 then is cooled to maintain the desired reaction temperature by circulating a cooling medium, e.g., cooling tower water, through the cylindrical passageway disposed adjacent to a portion of the inner process wall 28 that is adjacent to the rotor blades 30. While FIGS. 3A and 3B show a single heating or cooling medium 36 circulating through the cylindrical passageway, it is understood that two non-interconnected passageways can be included (not shown)—one for a heating medium to bring the temperature of the reactants up to reaction temperature and a separate passageway for cooling medium to maintain isothermal conditions within the thin-film reactor. Upon reaching reaction temperature, circulation of heating medium would be ceased and circulation of cooling medium would begin. As described earlier, the epoxidation reaction forms an oxirane ring at one or more double bonds contained in the unsaturated substrate reactant entering the thin-film reactor 10 through feed conduit 14.

The rotor blades 30 provide a turbulent thin-film in contact with the heated, smooth inner process wall 28. The thin-film of reactants are in contact with the process wall 28 at all times, regardless of the feed rate of reactants and evaporation rates of water and acid. This thin-film of reactants is constantly renewed as the progressively more concentrated material is displaced towards the bottoms product discharge conduit 22 by the incoming reactants. Vacuum, e.g., 25 to 400 mm Hg absolute, may be maintained in the thin-film reactor 10 to minimize the processing temperature, enhance removal of water and increase the rate of reaction. As the residence time is generally measured in seconds, the degradation of heat sensitive materials is minimized.

The preferred molar ratios of reactants are about 0.5–1.0 to about 1.0–0.05, more preferably about 0.9–1.0 to about 1.0–0.5, and most preferably from about 1.1:1.0 to about 1.0–0.9, especially 1:1, unsaturated reactant to peroxide. Lower amounts of peroxide can provided for desired amounts of unsaturation in the epoxidized product. The molar ratio of organic acid to peroxide is about 2:1 to about 1:1. The ratio of the mineral acid to hydrogen peroxide is low at about 0.20 to about 0.50 pounds per 100 pounds. The feed rates are dependent upon the desired production volume of the epoxidized products The feed rates can also be adjusted to control the rate of reaction and product quality.

We claim:

1. A method of epoxidizing an unsaturated compound having a carbon-to-carbon double bond to form an oxirane ring across the double bond comprising:
    adding to said unsaturated compound (a) an organic acid capable of being oxidized to form a peracid; (b) an oxidizing agent selected from hydrogen peroxide or acetaldehyde monoperacetate, or a combination thereof; and (c) with or without an acid catalyst selected from a mineral acid or styrene sulfonic acid, or a combination thereof to form a reactant mixture; and
    forming the reactant mixture in a film against a wall of a thin-film reactor that is at a temperature sufficient to form a peracid from the organic acid, and contacting the film of reactant mixture against the film reactor wall for a time sufficient for reaction of a portion of the peracid with the unsaturated compound to form an oxirane ring across a double bond of the unsaturated compound.

2. A method in accordance with claim 1, wherein the method is a continuous method such that the reactant mixture is continuously fed to the thin-film reactor and the epoxidized unsaturated compound is continuously recovered from the thin-film reactor while maintaining the thin-film reactor under isothermal conditions.

3. A method in accordance with claim 2, further including the step of recovering (a) and (b) and water from the thin-film reactor for recycle of (a) and (b) to the thin-film reactor together with feeding to the thin-film reactor additional unsaturated compound and additional (a), (b), and (c) in amounts sufficient for epoxidizing the additional unsaturated compound.

4. A method in accordance with claim 1, wherein the film of reactants is heated or cooled to a temperature in the range of about 65° F. to about 150° F.

5. A method in accordance with claim 1, wherein the molar ratio of unsaturated compound to peroxide are in the range of 0.5–1.0 to 1.0–0.05.

6. A method in accordance with claim 2, further including the step of continuously forcing the reactant mixture against said heated reactor wall, by centrifugal force, for efficient heating, in film form, of the reactant mixture.

7. A method in accordance with claim 2, further including the additional step of recycling non-epoxidized and/or incompletely epoxidized unsaturated compound to the film reactor for epoxidation of at least a portion of the non-epoxidized and/or incompletely epoxidized unsaturated compound.

8. A method in accordance with claim 1, wherein the feed rates of unsaturated compound, and peroxide can be varied to affect production rates and product quality.

9. A method in accordance with claim 8, wherein the residence time in the film reactor is in the range of 1 second to 300 seconds.

10. A method in accordance with claim 9, wherein the residence time in the film reactor is in the range of 3 seconds to 30 seconds.

11. A method of epoxidizing an unsaturated compound having a carbon-to-carbon double bond to form an oxirane ring across the double bond comprising:

adding a peracid and said unsaturated compound to a thin-film reactor to form a reactant mixture in a film against a wall of the thin-film reactor that is at a temperature sufficient for reaction of a portion of the peracid with the unsaturated compound to form an oxirane ring across a double bond of the unsaturated compound.

12. A method in accordance with claim 11, wherein the method is a continuous method such that the reactant mixture is continuously fed to the thin-film reactor and the epoxidized unsaturated compound is continuously recovered from the thin-film reactor while maintaining the thin-film reactor under isothermal conditions.

13. A method in accordance with claim 12, further including the step of recovering excess acid from the thin-film reactor for peracid manufacture and feeding the manufactured peracid to the thin-film reactor together with feeding to the thin-film reactor additional unsaturated compound, and additional peracid in an amount sufficient for epoxidizing the additional unsaturated compound.

14. A method in accordance with claim 13, wherein the film of reactants is heated or cooled to a temperature in the range of about 65° F. to about 150° F.

15. A method in accordance with claim 11, wherein the molar ratio of unsaturated compound to peracid is in the range of 0.5–1.0 to 1.0–0.05.

16. A method in accordance with claim 11, further including the step of contacting an organic acid, and an oxidizing agent for the organic acid, with an ion-exchange resin to form a peracid by oxidation of the organic acid and feeding the peracid to the thin-film reactor for reaction with the unsaturated compound.

17. A method in accordance with claim 12, further including the step of continuously forcing the reactant mixture against said heated reactor wall, by centrifugal force, for efficient heating, in film form, of the reactant mixture.

18. A method in accordance with claim 12, further including the additional step of recycling non-epoxidized and/or incompletely epoxidized unsaturated compound to the thin-film reactor for epoxidation of at least a portion of the non-epoxidized and/or incompletely epoxidized unsaturated compound.

19. A method in accordance with claim 11, wherein the residence time in the thin-film reactor is in the range of 1 second to 300 seconds.

20. A method in accordance with claim 19, wherein the residence time in the film reactor is in the range of 3 seconds to 30 seconds.

* * * * *